United States Patent
Caillouette (10) Patent No.: US 6,283,927 B1
(45) Date of Patent: Sep. 4, 2001

(54) ESTROGEN OR ESTRADIOL NEED DETERMINATION BY VAGINAL OR URETHRAL ACIDITY DETERMINATION

(76) Inventor: James C. Caillouette, 685 Oak Knoll Cir., Pasadena, CA (US) 91106

( * ) Notice: Subject to any disclaimer, the term of this patent is extended or adjusted under 35 U.S.C. 154(b) by 0 days.

(21) Appl. No.: 09/258,381

(22) Filed: Feb. 26, 1999

Related U.S. Application Data (60) Division of application No. 08/890,748, filed on Jul. 11, 1997, now Pat. No. 5,916,176, which is a continuation-in-part of application No. 08/699,251, filed on Aug. 19, 1996, now Pat. No. 5,735,801, which is a continuation-in-part of application No. 08/570,534, filed on Dec. 11, 1995, now Pat. No. 5,762,614, which is a continuation-in-part of application No. 08/537,379, filed on Oct. 27, 1995, now Pat. No. 5,577,512, which is a continuation-in-part of application No. 08/295,399, filed on Aug. 25, 1994, now Pat. No. 5,425,377.

(51) Int. Cl.⁷ ........................................................ A61B 5/00
(52) U.S. Cl. .................................................................. 600/584
(58) Field of Search .................................... 600/573, 584, 600/591, 551

(56) References Cited

U.S. PATENT DOCUMENTS

| | | |
|---|---|---|
| 2,664,879 | 1/1954 | Hardy . |
| 2,945,491 | 7/1960 | Gibbs . |
| 3,037,496 | 6/1962 | Melges . |
| 3,117,569 | 1/1964 | Wegner . |
| 3,319,621 | 5/1967 | Schwerin . |
| 3,507,269 | 4/1970 | Berry . |
| 3,509,872 | 5/1970 | Truhan . |
| 4,820,259 | 4/1989 | Stevens . |
| 4,862,899 | 9/1989 | Bucaro . |
| 5,063,930 | 11/1991 | Nucci . |
| 5,147,288 | 9/1992 | Schiavo . |

FOREIGN PATENT DOCUMENTS

WO-A-97/46878  12/1997 (WO).

OTHER PUBLICATIONS

"Vulvovafinitis", vol. 1, Chapter 37, Ronald M. Meltzer.
"Urinary Incontinence and Related Urogenital Symptoms in Elderly Women", Ulla Molander, Scandinavian Association of Obstetericians and Gynecologists, Supplement 158, vol. 72, 1993.
"Estrogen Deprivation and Vaginal Function in Postmenopausal Women", James P. Semens, MD, Gorm Wagner, MD. Peter Smith, Dept. of Pbstetrics & Gynecology, University Hospital, S-751 85 Uppsala, Sweden "Estrogen and the Urogenital Tract".
Gloria Bachmann, Maturitas 22 Suppl. (1995) S21–S29 "The Estradiol Vaginal Ring—A Study of Existing Clinical data".

*Primary Examiner*—Max Hindenburg
(74) *Attorney, Agent, or Firm*—William W. Haefliger

(57) ABSTRACT

In the method of determining need for human estrogen replacement therapy or estrogen or estradiol dose change, the steps include determining local acidity proximate a moist wall surface of the vagina, or urethra, as differing from desired threshold level (pH 4.5), and administering sufficient estrogen or estradiol to result in change in acidity toward such level.

6 Claims, 6 Drawing Sheets

ESTROGEN OR ESTRADIOL NEED DETERMINATION BY VAGINAL OR URETHRAL ACIDITY DETERMINATION

This application is a divisional of U.S. Ser. No.08/890,748 filed Jul. 11, 1997, now U.S. Pat. No. 5,916,176 which is a continuation-in-part of prior U.S. application Ser. No. 08/699,251 filed Aug. 19, 1996 now U.S. Pat. No. 5,735,801 which is a continuation-in-part of prior U.S. application Ser. No. 08/570,534 filed Dec. 11, 1995, now U.S. Pat. No. 5,762,614, which is a continuation-in-part of prior U.S. application Ser. No. 08/537,379 filed Oct. 27, 1995, now U.S. Pat. No. 5,577,512, which is a continuation-in-part of prior U.S. application Ser. No. 08/376,830 filed Jan. 23, 1995, now U.S. Pat. No. 5,664,579, which is a continuation-in-part of prior U.S. application Ser. No. 08/295,399 filed Aug. 25, 1994, now U.S. Pat. No. 5,425,377.

BACKGROUND OF THE INVENTION

This invention relates generally to factors involved in determining estrogen or estradiol administration to human females, and more particularly to a simple and effective method and means to effect such determination such as need for beginning estrogen replacement therapy or changes in dosage of estrogen or estradiol.

There is need for improvements in methods to determine whether or not a human female should be administered estrogen or estradiol or needs a higher or lower dose of estrogen or estradiol. The present invention addresses that need.

SUMMARY OF THE INVENTION

It has been discovered that the acidity (pH) or pH(acidity) level of a moist wall surface of the vagina or urethra can be employed in estrogen or estradiol need determination. In accordance with the invention, the method of determining need for estrogen or estradiol increase or decrease includes the steps:

a) determining local acidity proximate a moist wall surface of the vagina, or urethra, as differing from desired threshold level, and in the substantial absence of bacterial vaginosis, or other contaminants such as medications, blood, semen, b) and administering sufficient estrogen or estradiol to result in change in acidity toward such level or a pH of about 4.5 without menopausal signs or symptoms.

Typically, administering of sufficient estrogen or estradiol may be effected on a periodic regular basis, as for example increased or decreased dosage (for example orally) on a daily basis, and in increasing amounts, and said determination of local acidity is repeated, whereby said local acidity is ultimately determined to have reached said desired level.

Yet another object is the carrying out of such determination of local acidity as by employing an acidity indicator, for contacting the wall surface of the vagina or urethra. Such an indicator may desirably include one of the following:

i) NITRAZINE® paper
ii) phenaphthazine on a carrier
iii) a material or materials exhibiting different colorations or other indicators as a function of pH level.

A strip of material may be used to carry the indicator, and such a strip may be employed in contacting the vaginal or urethral wall. One method of use is to provide the strip of material on an applicator, an example being a carrier stick which is easily manipulable.

A further object is to provide a pH level indicator comprising a material or materials exhibiting colorations corresponding to pH levels of moisture of the wall surface of the vagina, or urethra, said colorations being different for different pH levels. The desired threshold level of acidity is approximately 4.2–4.5.

Yet another object is to provide a method that includes the steps:

a) providing an acidity sensing means on a carrier, b) providing a protective porous layer adjacent said sensing means, c) manipulating the carrier proximate vaginal moisture, and including allowing vaginal and/or urethral moisture to penetrate said porous layer for contact with said sensing means, d) and detecting a vaginal and/or urethral moisture produced change in said sensing means for determining need for beginning estrogen replacement therapy or a change in estrogen or estradiol dose to be administered to a human female.

An additional object is to measure vaginal or urethral pH for screening purposes, a vaginal or urethral pH level of 4.5 being consistent with a physiologic serum estradiol and the absence of bacterial vaginosis. An elevated vaginal pH in the 5.0–6.5 range suggests a diagnosis of either bacterial vaginosis or decreased serum estradiol. In patients with an elevated pH, vaginal culture should establish the diagnosis. In the absence of vaginosis, a vaginal pH of 6.5–7.5 is strongly suggestive of a low serum estradiol or menopause. Titration of estradiol level by vaginal or urethral pH during estrogen replacement therapy is then carried out.

These and other objects and advantages of the invention, as well as the details of an illustrative embodiment, will be more fully understood from the following specification and drawings, in which:

DETAILED DESCRIPTION

As referred to, the method of the invention concerns determining need for estrogen replacement therapy or estrogen or estradiol dose change, through vaginal wall moisture pH determination or urethral wall moisture pH determination. Typical steps include:

- a) determining local acidity proximate a moist wall surface of the vagina or urethra, as differing from desired threshold level, as in the substantial absence of bacterial vaginosis, or other contaminants such as medication, blood, semen,
- b) and administering sufficient estrogen or estradiol to result in change in said acidity toward said level.

A more complete method includes:

- a) first determining local acidity proximate a moist wall surface of the vagina, said determining employed as an indicator of the presence or absence of bacterial vaginosis,
- b) and, after a vaginosis condition has been treated and eliminated, then again determining local acidity proximate a moist wall surface of the vagina, as differing from desired threshold level,
- c) and administering sufficient estrogen or estradiol to result in change in said acidity toward said threshold level.

Figure 13:
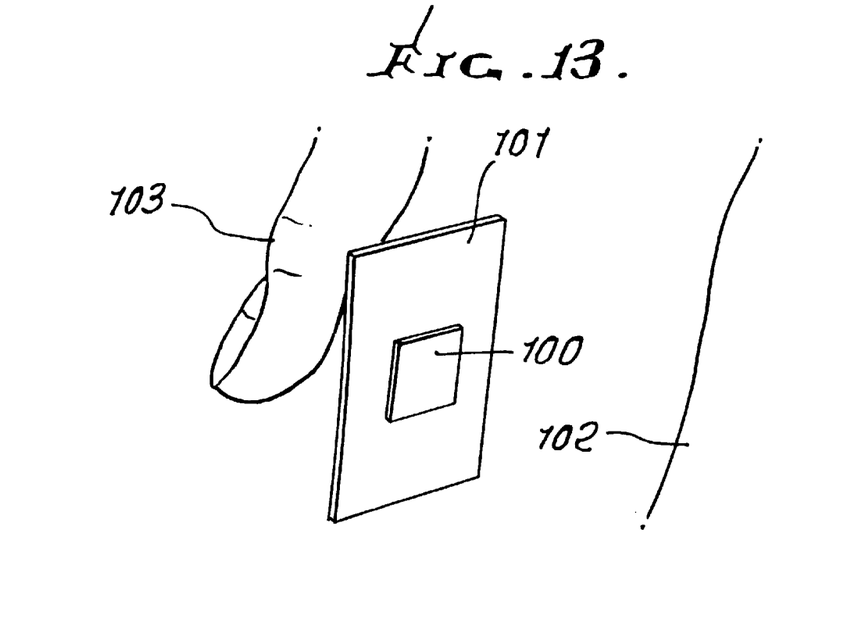
FIG. 13 is a perspective view showing pH indicator manipulation manually.
Figure 14:
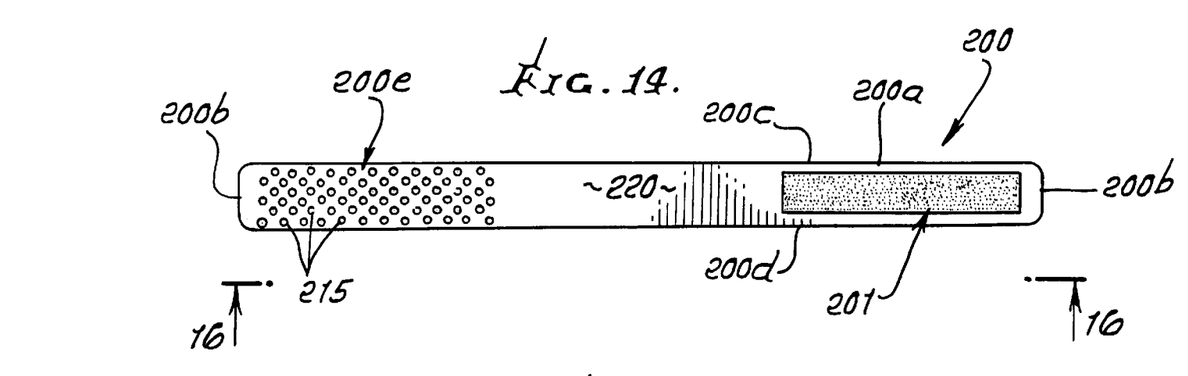
FIG. 14 is a plan view of the top side of a modified stick apparatus.
Figure 15:
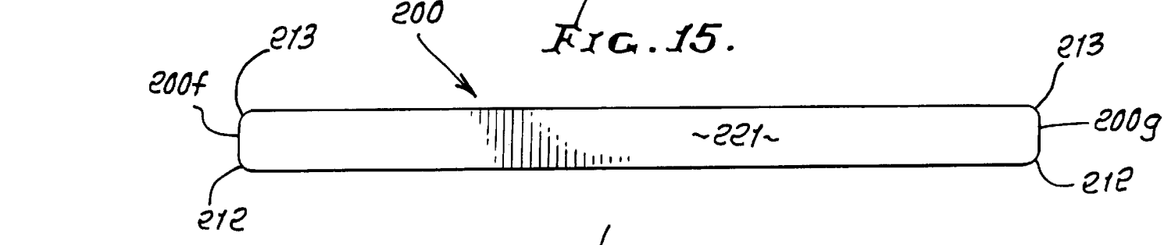
FIG. 15 is a plan view of the bottom side of the FIG. 14 stick apparatus.
Figure 16:
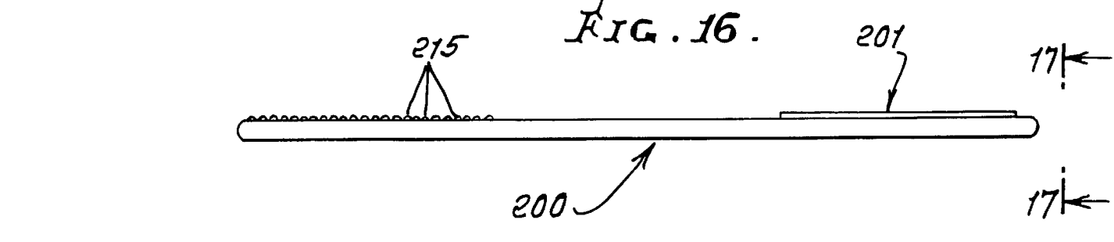
FIG. 16 is an edge view taken on lines 16—16 of FIG. 14.

A pH indicator 100, as seen in FIG. 13 may be employed, and that indicator may be located on a carrier strip 101, which is easily manipulable into contact with the vaginal or urethral wall, shown at 102, the user's finger shown at 103 to urge the tissue strip toward the wall surface. Such an indicator may take the form of one of the following, although other indicators are usable.

i) NITRAZINE® paper
ii) phenaphthazine on a carrier
iii) a material or materials exhibiting different colorations or other indicators as a function of pH level.

The indicator may desirably exhibit different colorations or changes corresponding to different pH levels, of moisture at the vaginal or urethral wall, and from which the observed coloration or changes may be used to indicate need for greater or lesser estrogen or estradiol dosage, as on a daily or other periodic basis. In the case of NITRAZINE® paper (phenaphtazine), the correlation of pH to color is as follows:

| pH | Color |
| --- | --- |
| 4.5 | golden yellow |
| 5.0 | beige |
| 5.5 | light olive |
| 6.0 | dark olive |
| 6.5 | olive blue |
| 7.0 | purple blue |
| 7.5 | dark blue |

In a typical example, if the user detected or determined an indicator color of dark olive, it would be determined that an estrogen or estradiol increase above the existing daily level of use would be recommended, in order to diminish pH level to 4.2 to 4.5 within one to two weeks, for example. Testing would be performed on a once a week basis. Thus, if the user had been taking 1 mg. of estrogen or estradiol per day, for example orally, she would be recommended to increase that level to 1.5 mg. per day, the objective being to reduce the pH level to about 4.5 within about 10–21 days. If the tested color were not golden yellow (p4.5 pH) after 7–8 days, the dosage might be increased to 2.0 mg. level, per day, until a golden yellow color of the test strip was achieved. Thus, pH determination is indicative of need for change in estrogen or estradiol dosage (up or down).

The indicator may alternatively be employed on a manipulable apparatus, as for example a carrier stick. In FIGS. 1–4, an elongated, narrow carrier stick 10 may consist of wood, plastic, or other material. Provided on the carrier stick are:

a pH indication means, as generally shown at 11, at one end portion 10*a* of the stick; and a color comparison pH measurement means, as generally indicated at 12, spaced from stick end portion 10*a*, but close to 11;

As shown, the first means 11 may comprise a pH indication strip, such as a NITRAZINE® (Phenaphthazine) strip, wound about the stick end portion 10*a* and adhered to same as by an adhesive. NITRAZINE® (Phenaphthazine) strips are products of Bristol-Myers Squibb. The color comparison pH measurement means 12 may comprise a thin paper strip adhered to the stick surface to extend lengthwise of the stick from the edge or end 11*a* of the first means 11. The second means is shown to have color gradations in a series sequence, as in colored bands 12*a*, positioned lengthwise of or along the stick. In addition, the paper strip 12 may include pH numerical indicators 12*b* along side the color gradation bands, to enable:

visual color comparison of the pH indication means 11 (immediately after its exposure to vaginal or urethral fluid or moisture) with the bands 12*a*, for visual selection of that band most close in color to the color of the indication means 11;

and immediate visual readout of the pH number adjacent the selected band.

Such readout of pH is then compared with the desired level of about 4.2–4.5 to enable determination of a recommended dosage of estrogen or estradiol, as on a daily basis.

Figure 1:
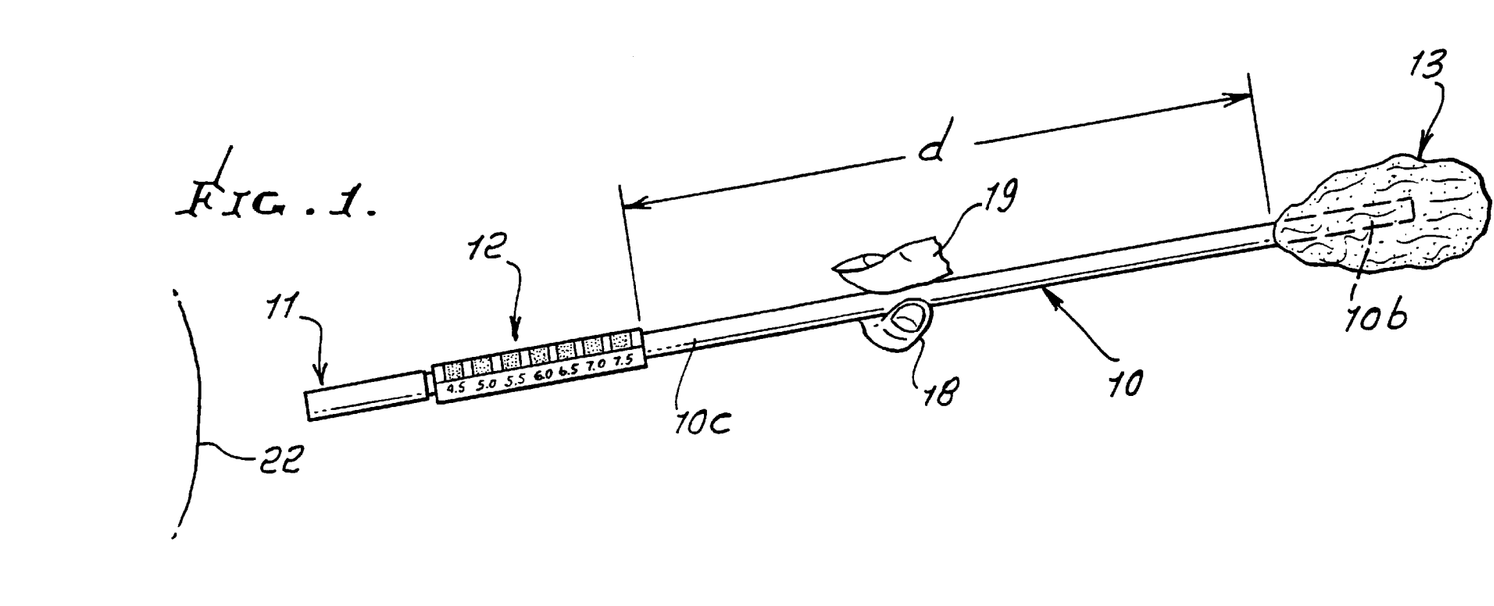
FIG. 1 is a side elevational view of stick apparatus incorporating the invention.

The stick projects freely at 10*c* away from the first and second means 11 and 12 for manual manipulation (see the grasping finger and thumb 18 and 19), to first obtain pH indication of vaginal or urethral wall moisture at one end of the stick, and to enable visual interpretation of that indication by color comparison with the second means, without manual release of the stick. The stick is then disposable, or may be disposed of.

Lengthwise spacing "d" between 12 and stick end 10*d* is such as to enable free manual manipulation of the stick; and such spacing is typically between 3 and 5 inches, enabling ready finger grasping of the stick and manipulation thereof. In a specific example, "d" is about 4 inches, and the stick diameter or width is about 3/16 to 3/8 inch.

The method of measuring pH of vaginal moisture includes the steps:

- a) providing a pH indicator on a carrier stick,
- b) manipulating the stick to obtain pH indication of vaginal or urethral wall moisture at said indicator, c) visually interpreting that indication to determine need for a change in estrogen or estradiol dosage, d) and disposing of the stick, The overall sizes of 11, 12 and 13 are such as to enable ready insertion into the vagina, or urethra, or application to a surface of the vagina or urethra, via stick manipulation at zone 10c.

Figure 5:
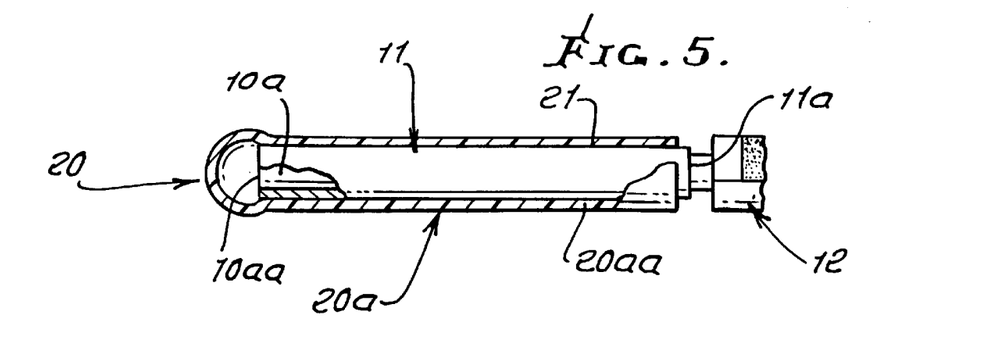
FIG. 5 is an elevation, partly in section, showing a modification.
Figure 6:
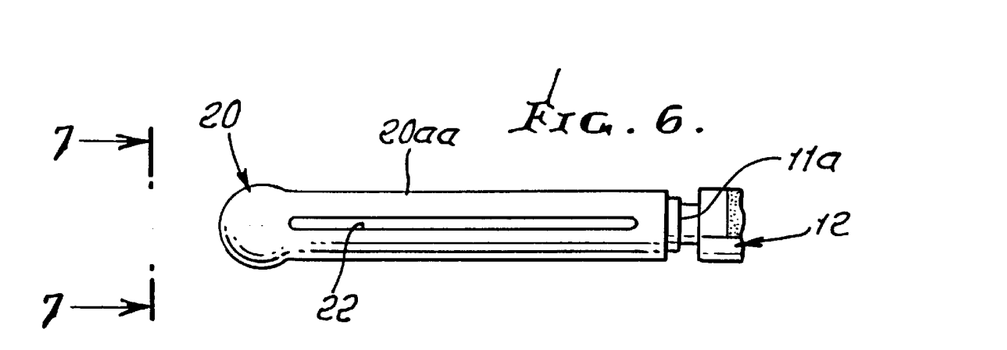
FIG. 6 is a side elevation of the FIG. 5 modification.
Figure 7:
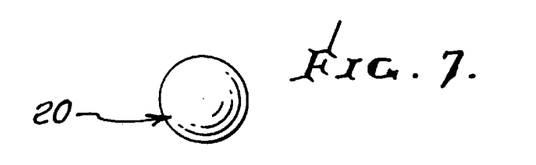
FIG. 7 is an end view taken on lines 7—7 of FIG. 6.

Referring now to the modification shown in FIGS. 5–7, a smooth surfaced protective tip 20 is provided to face endwise at the end 10aa of the stick end portion 10a. As shown, the tip 20 is endwise convex, as for example bulbous, to provide for or enable comfortable insertion of the stick end portion 10a into the vagina or urethra, for pH measurement. The tip 20 may typically be formed integrally with a sleeve 20a assembled over and closely fitting the measurement strip 11, and may be suitably adhered thereto, locally, as at 21. A suitable bonding agent is epoxy. The remainder of the strip 11 is therefore available for pH indication. Alternatively, the sleeve may be attached, as by heat shrinking, or by wedge fit.

A fluid access opening is provided through the wall of the sleeve, whereby vaginal moisture or fluid may access the strip 11 via that opening. See for example elongated slot 22 in the sleeve wall 20aa. The sleeve and tip may consist of transparent, molded, plastic material, to facilitate viewing of a change of color of the strip 11.

Figure 8:
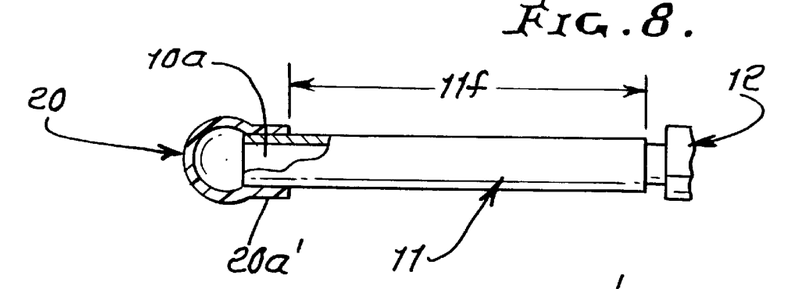
FIG. 8 is an elevation showing a further modification.

In FIG. 8, the sleeve 20a is shortened and attached at sleeve end 20a' into flush, or near flush, relation with the surface of the strip, at a locus on stick end portion 10a. This leaves the remaining length 11f of the strip openly exposed for moisture contact.

Figure 9:
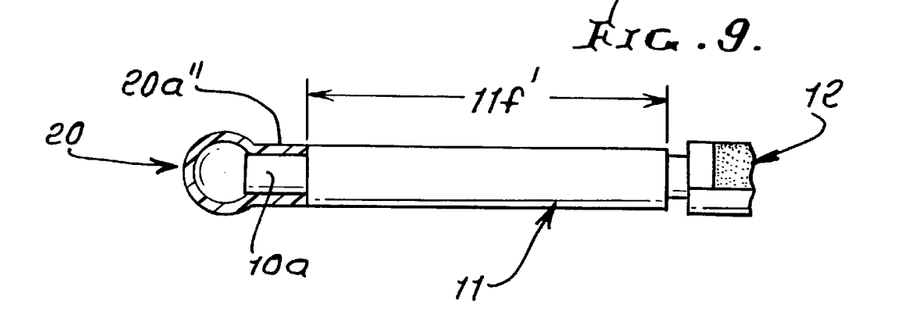
FIG. 9 is an elevation showing yet another modification.

In FIG. 9, the sleeve 20a" is also shortened and attached to the stick end portion 10a, and in endwise alignment with the strip 11. This also leaves the remaining length 11f' of the strip openly exposed for moisture contact.

Figure 2:
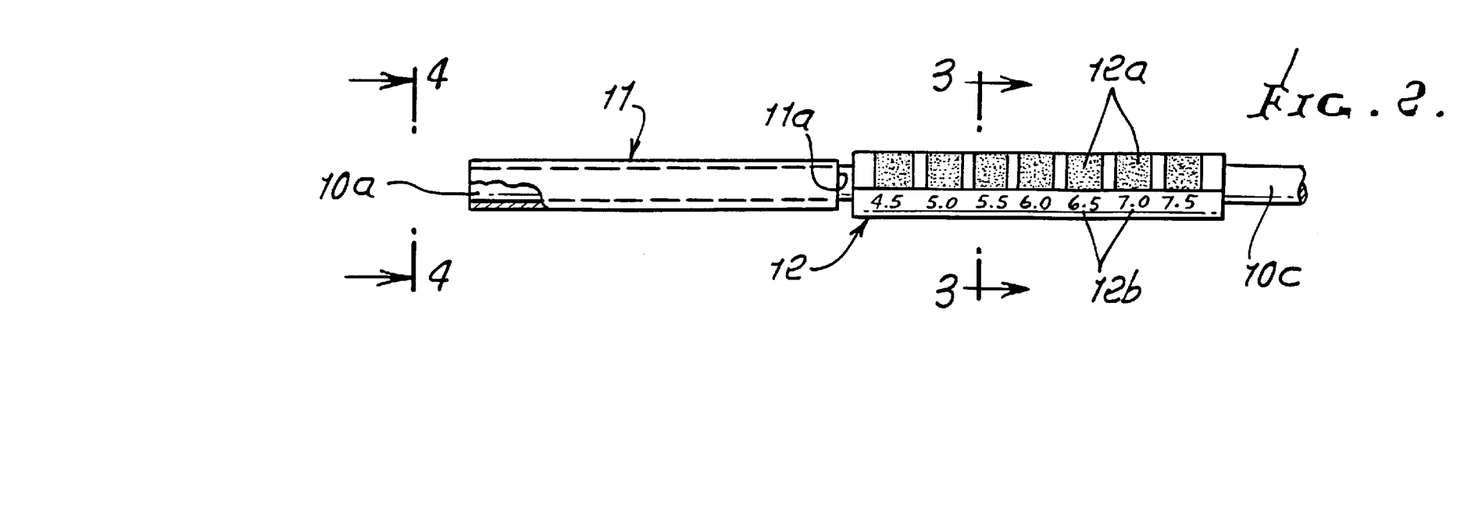
FIG. 2 is an enlarged side view of one end portion of the FIG. 1 stick apparatus.
Figure 3:
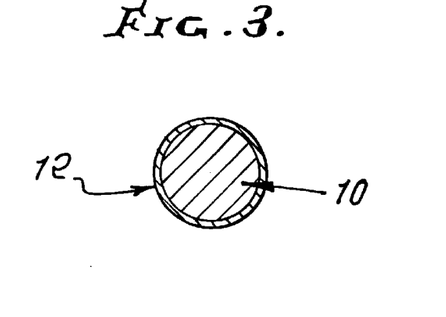
FIG. 3 is an enlarged section taken on lines 3—3 of FIG. 2.
Figure 4:
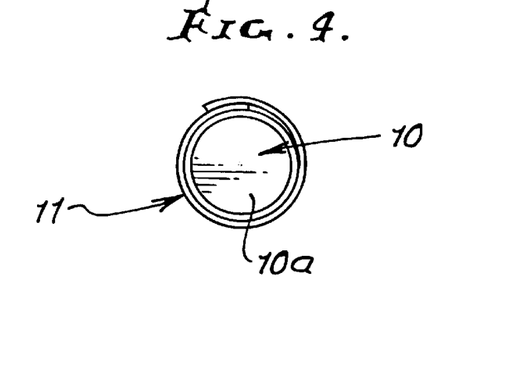
FIG. 4 is an enlarged end view taken on lines 4—4 of FIG. 2.
Figure 10:
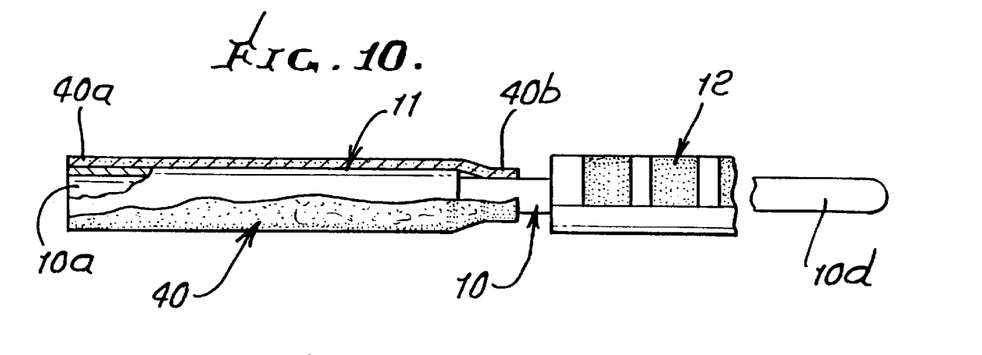
FIG. 10 is a view like FIG. 2, showing a protective porous layer applied over a pH indicator strip.

Referring now to the modification seen in FIG. 10, the elements the same as in FIG. 2 are given the same numerals. In addition a protective layer 40 in the form of a thin porous barrier, is applied adjacent the outer side of strip 11 so as to cover the latter (i.e. extend thereabout) and to be carried by the stick. Layer 40 allows vaginal moisture to penetrate through it and to contact the pH indicator strip 11, as during a test. Following the test, the strip 11 may be observed as described above, and for this purpose the layer 40 may be at least partly removed from adjacency to the strip, as by complete manual removal. Opposite end portions 40a and 40b of layer 40 may be initially attached as by light bonding or sticking to the ends of the strip 11, or to the stick, allowing pull-away removal of the layer at the end of the test. Such bonding agents are known, as on 3M Micropore Tape. Layer 40 acts as a barrier, during a test, to block direct contact of vaginal tissue or urethral tissue with strip 11, preventing any possible irritation of such tissue.

Figure 11:
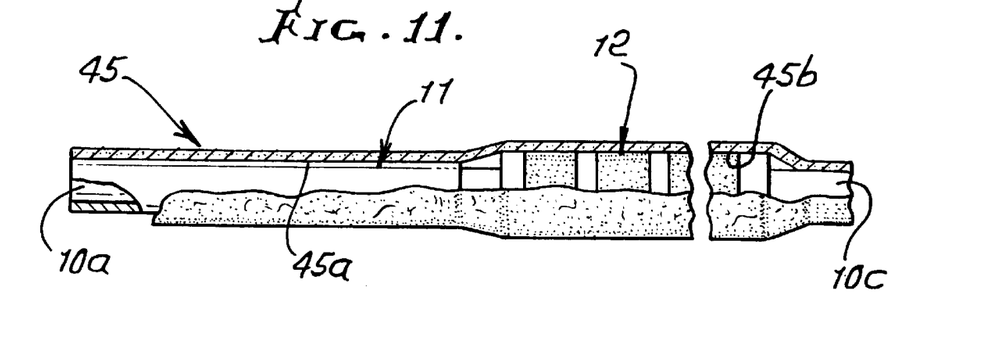
FIG. 11 is a view like FIG. 10, but showing the protective layer also applied over the color comparison measurement means.

In FIG. 11, the elongated layer 45 is like layer 40, but also extends over and about the color comparison measurement means 12, and is adhered, as described above, to the elements 11 and 12, as at 45a and 45b to completely cover 11 and 12 as during a test, while allowing pull-away of the layer 45 for visual observation of 11 and 12 after the test. Either one or both of 11 and 12 may be considered as a pH detecting means.

Figure 12:
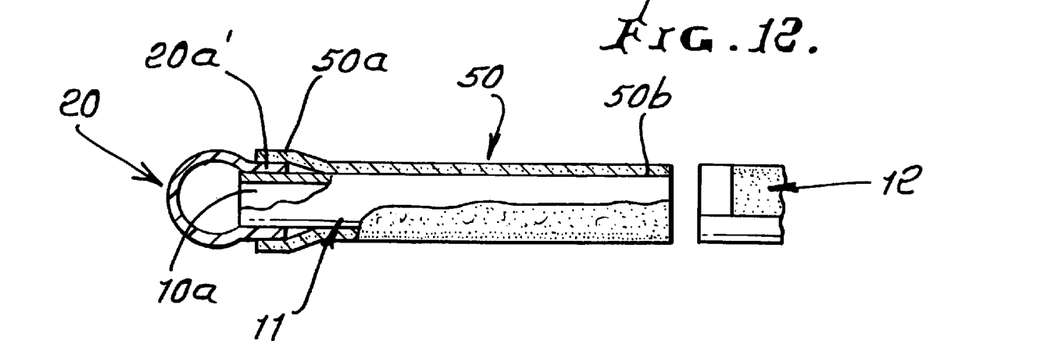
FIG. 12 is a view like FIG. 8, showing a protective porous layer applied over a pH indication strip.
Figure 12A:
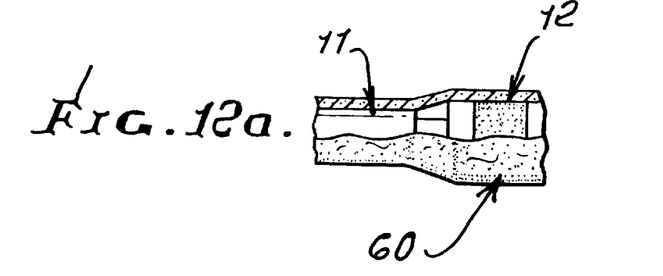
FIG. 12a is a view like FIG. 12, but showing the protective porous layer extending over the color comparison measurement means.

FIG. 12 is like FIG. 8, but layer 50 corresponding to layer 40 has its end 50a adhered to and about the sleeve 20a', while end portion 50b is adhered to the right end of strip 11, as shown. Note smooth surfaced blunt knob 20, as referred to above.

FIG. 13 is like FIG. 12, except that the layer 60, corresponding to 50, is elongated to cover the color comparison measurement means 12, and to adhere at 60b to the rightward end of 12.

In FIGS. 10–12a, the porous barriers, as at 40, 45, 50 and 60 may consist of one or more barrier tissue layers, as for example are used in incontinence pads. One example is the outer layer of the Kimberly Clark product NEW DEPEND. Another usable barrier is the 3M product known as MICROPORE tape. One side of such tape is "tacky", i.e. weakly adhesive, so that it will adhere along the tape length to the elements 11 and/or 12 referred to. Barriers 45 and 50 as referred to may comprise such tape material.

In FIGS. 14–17, a modified elongated, narrow carrier stick 200 may consist of wood, plastic or other carrier material. A pH indication strip 201 such as phenaphthazine paper is adhered to one substantially flat side 200a of the stick 200, and near one end 200b, as by an adhesive. The strip 201 is elongated, and spaced from opposite edges 200c and 200d of the stick, as well as from end 200b. Typically, rectangular strip width is about .025 inches, and its length is about 1.5 inches. The stick width is about .0375 inches, its length is about 5 inches and its thickness is about .0125 inches.

Figure 17:
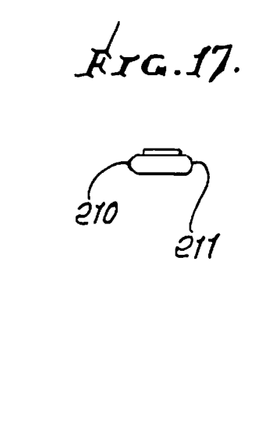
FIG. 17 is an end view taken on lines 17—17 of FIG. 16.

The stick edges 200c and 200d are convexly curved or rounded as at 210 and 211 in FIG. 17. Also, the stick opposite ends 200f and 200g are convexly curved or rounded as at 212 and 213.

The handle portion 200e of the stick is desirably textured, as by provision of dimples 215 on side 200a of the stick. The length of such texturing may be about 1.5 inches, from end 200b. Such texturing aids finger and thumb gripping of the handle portion for accurate stick manipulation to position strip 201 adjacent the vaginal wall. Aiding of manipulation of the paper strip is enhanced by locating the texturing and paper strip at the same side of the stick. Note that the stick preferably has smooth top surface extent at 220 between 215 and 201, and also a smooth bottom surface at 221.

Figure 18:
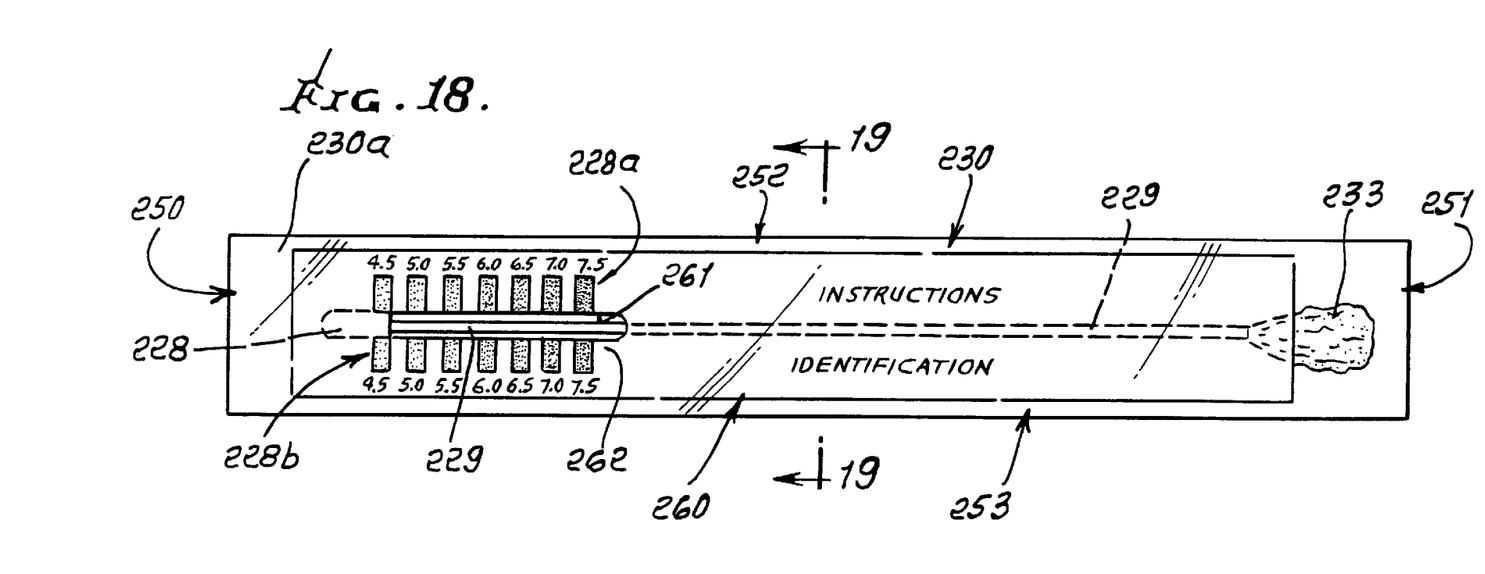
FIG. 18 is a plan view of modified apparatus.
Figure 19:
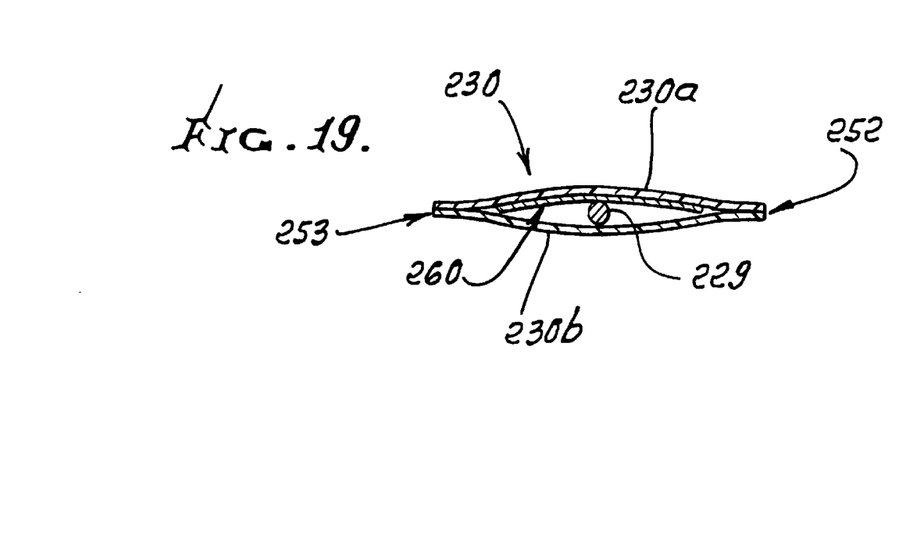
FIG. 19 is an enlarged section taken on lines 19—19 of FIG. 18.

FIGS. 18 and 19 show yet another and preferred kit in which an indicator strip or tip 228 (corresponding to strip or tip 111) is carried at the left end of elongated stick 229. A swab 233 is carried at the right end of the stick. An encapsulating, thin, flexible, transparent receptacle 230 protectively contains the elongated stick, tip 228 and swab 233, and may be torn open to retrieve the stick. The receptacle may consist of thin walled plastic sheets 230a and 230b bonded together along sheet edge portions indicated at 250, 251, 252 and 253, whereby the receptacle is sealed.

A thin, elongated paper insert sheet 260 is also received in the receptacle, to overlie most of stick 200, whereby use instruction and identification data may be printed on the sheet 260 and presented upwardly or outwardly for viewing through the transparent upper sheet 230a. Sheet 260 defines a narrow window or cut-out at 261, which is elongated along a mid-portion 262 of sheet 260, as shown.

Color comparison elements such as bands are carried by the insert sheet 260, as in two rows shown at 228a and 228b, at opposite sides of the window. Preferably, the longitudinally spaced bands extend to laterally spaced edges of the window, for ease of color comparison of the indicator (after its exposure to moisture as described above) with the different bands. Sheet 260 may be eliminated, and the bands printed or affixed on the receptacle top sheet, to define the window.

Longitudinally spaced bands have different colors, while laterally oppositely spaced bands have the same color. Note their pH numerical labeling, at 4.5, 5.0, 5.5, 6.0, 6.5, 7.0, and 7.5, along the window length.

In use, the right end of the receptacle is opened, and the carrier stick 229 is withdrawn, for use. Thereafter, the indicator tip 228, which may be cylindrical, after its exposure to moisture, is re-inserted into the elongated receptacle 230, under the insert sheet 260, to bring tip 228 under the window 261. Tip 228 preferably has a width or diameter greater than the window width, so that it adjacently registers with the successive bands in the two rows as the tip moves longitudinally. This facilitates ease of color comparison use. The tip and stick remain in the receptacle, for ease of disposal.

In addition to provision and manipulation of a first carrier stick as referred to, with respect to vaginal or urethral moisture samples, the method may also include providing an elongated second carrier having a second pH detector on that carrier at an end position thereof, and manipulating the second carrier to effect exposure of the second detector to vaginal or urethral moisture, thereby to cause the second detector to exhibit a color change, and comparing the color changes exhibited by the first and second detectors. If color changes exhibited (due to both vaginal and urethral moisture contact with the detector) are the same, a validity check is thereby provided.

Accordingly, the method of determining validity of pH of body moisture or fluid may include:

a) determining pH of vaginal moisture or fluid, by employment of a first indicator, b) also determining pH of urethral moisture or fluid, by employment of a second indicator. The two indicators may then be compared, as for example by comparison of color changes produced on or by the indicators. The indicators themselves would be identical as to color change capability.

EXAMPLES

OBJECTIVES

To confirm the elevation of vaginal pH expected in patients with bacterial vaginosis and to examine the relationship of serum FSH and estradiol levels to vaginal pH in normal patients without vaginosis.

STUDY DESIGN 2,038 patients in a solo private practice underwent measurement of vaginal pH during routine pelvic examinations. 201 of these patients were chosen at random for this study. Measurements were made of serum levels of FSH and estradiol. Vaginal cultures were taken from 83 patients. Specimens were sent to a single commercial laboratory. Vaginal pH was determined by phenaphthazine (NITRAZINE®) pH paper. Vaginal pH was correlated with serum FSH, estradiol levels, and vaginal cultures using statistical analysis.

RESUTLTS

Vaginal pH was elevated in patients with documented vaginosis. Serum estradiol levels showed an inverse and serum FSH levels showed a direct statistical correlation with vaginal pH.

MATERIALS AND METHODS

Between May 1995 and May 1996, 2,038 patients in a private gynecologic practice were tested for vaginal pH. None of the patients were pregnant.

A total of 83 patients had vaginal cultures to study the effect of vaginosis on vaginal pH.

Two hundred one patients were tested for vaginal pH, serum FSH and serum estradiol. Of these 201 patients, 100 were on Estrogen Replacement Therapy and 8 were on oral contraceptives. Ninety-three patients were on no hormonal treatment. No patients tested were using vaginal medication.

Eighteen patients were tested for vaginal pH, serum FSH and serum estradiol on two separate occasions. Nine of these patients were tested before and after the use of estrogen. Nine patients were tested after a change in estrogen dose. In all nine cases, the estrogen does was increased. This separate study was done to observe the change in vaginal pH, serum FSH and serum estradiol in response to a change in estrogen therapy.

Phenaphthazine (NITRAZINE®) pH indicator paper was used for vaginal pH testing (NITRAZINE® pH indicator paper pH 4.5 to 7.5 range, distributed by APOTHECON®, a Bristol-Myers Squibb Company, Princeton, N.J.). This pH paper has been used for vaginal pH testing since 1938. The extended range of pH 4.5 to 7.5 proved to be easier to read and more comprehensive for vaginosis and vaginal estrogen level. Other pH testing papers were tried. (Hydrion® pH papers, Micro Essential Laboratory, 4224 Avenue H, Brooklyn, N.Y. 11210 (718) 338-3618). (ColorpHast® pH test strips, EM Science, 480 Democrat Road, Gibbstown, N.J. 08027 (800) 222-0342).

The pH paper was applied directly to the lateral vaginal wall at the outer third of the vagina. Care was taken to avoid cervical mucous (pH 7.0), blood (ph 7.4), or other substances (such as semen pH 7.0–8.0) and lubricating jelly known to affect vaginal pH. All samples were interpreted in incandescent light for accuracy.

All vaginal cultures were collected using the Star Swab, Starplex Transport System and were sent to Unilab Corporation, Tarzana, Calif. Venopuncture for blood samples was obtained within one hour of the vaginal pH test. Serum FSH was run on the Dade/Baxter, Inc. Stratus II automated instrument and reported as miU/mL. Female normal ranges are: Follicular Phase: 3.6–16.0 miU/ml, Mid Cycle Peak: 8.1–28.9 miU/ml, Luteal Phase: 1.8–11.7 miU/mL and Post Menopausal: 22.9–167.0 miU/mL. Serum estradiol was determined by radio immune assay, using Diagnostics Products Corporation's Coat A Count and reported as pg/mL. The normal range is 10–375. All tests were done at Huntington Memorial Hospital laboratory, Pasadena, Calif. Statistical analysis was performed by using the computer program "Statistical Package for Social Sciences" (SPSS).

Relationships between vaginal pH, serum estradiol and FSH levels were evaluated using Spearmans's Correlation Coefficients. Treated and untreated groups were compared for these variables using t-tests and ANOVA with Duncan Multiple Comparisons. Paired t-tests were used to compare the difference in means due to initiation or change of estrogen therapy.

RESULTS

Of 84 patients who had vaginal cultures, 27 grew normal flora, 14 yeast, 15 Beta-hemolytic-streptococcus, 14 gardnerella, and 13 mixed pathogens. The mean pH of three subgroups with bacterial vaginosis is significantly higher than that obtained in patients with either normal flora or yeast infection (One way ANOVA, p<0.05). There was no significant difference in the vaginal pH among the three subgroups with bacterial vaginosis, and there was no significant difference between the pH in patients with yeast infection and those with normal flora.

In the overall group of 201 women tested for vaginal pH, estradiol and FSH, vaginal pH correlated positively with serum FSH levels and negatively with serum estradiol using Spearman's correlation coefficients.

When the group of 201 women was divided into those on estradiol therapy and those on no treatment, significant differences were found between mean vaginal pH, serum estradiol levels, and serum FSH levels. These differences were significant despite the inclusion of some apparently normally cycling women in the untreated group. There was no significant difference in the mean age of the patients between the two groups.

The characteristics of 18 women studied both before and after initiation (n=9) or change (n=9) of estrogen replacement therapy showed that serum estradiol levels increased and FSH levels decreased significantly after initiation or changes of dose of ERT (p<0.003 and p<0.001 respectively, using paired t-testing). There was a significant decrease in vaginal pH from 6.1±0.7 to 4.6±0.3 (p<0.001) in the group who went from no treatment to estrogen replacement. Mean vaginal pH also decreased, although to a lesser degree of significance, in the women who went from lower dose to higher dose ERT (p=0.05).

The data obtained support the well documented body of literature indicating that vaginosis results in an elevated vaginal pH (5.0–6.5). For this reason alone, vaginal pH should become a routine test during most speculum examinations. Women should be encouraged to do vaginal pH testing to alert both pregnant and non-pregnant women to the possibility of sub-clinical vaginosis and to seek medical advice for proper diagnosis and treatment. The combination of pH testing, vaginal culture, and treatment as indicated, have shown a decrease in premature rupture of membranes and premature delivery.

The editorial comments of Watson A. Bowes, Jr. in the May 1996 issue of Obstetrical and Gynecological Survey are pertinent.

Statistically significant is the fact that the vaginal pH level, in the absence of vaginosis, is a reasonable marker for most patient's estradiol status. In addition, an elevated vaginal pH level in a well estrogenized patient is a reasonable marker for vaginosis. In this regard, detected pH correlates positively (directly) with FSH; and pH correlates negatively (inversely) with estradiol intake.

In consideration of all that as been said, vaginal and/or urethral testing for pH level appears to be that hoped for, reliable, "low-tech" tool. It certainly complies with the mandate for cost-effective, improved health care.

In the above, estrogen or estradiol can be administered orally, intermuscularly, or vaginally.

I claim:

1. In the method of measuring pH of vaginal or urethral moisture for determination of need for change in estrogen or estradiol dosage, and employing apparatus which includes:
    a) a thin, flexible sheet carrier which is manipulable, and has opposite sides,
    b) pH indicating means on one side of the carrier, and sized for application to a zone adjacent the wall of the vagina or urethra,
    c) the carrier opposite side located for receiving manual pressure exerted to apply said pH indicating means to said wall, the method including:
        i) manually bringing said carrier and said pH indicating means into proximity to the wall of the vagina or urethra, and
        ii) manipulating said carrier, manually, to bring said pH indicating means into contact with the wall of the vagina or urethra,
    d) said opposite sides being flat and projecting away from the pH indicating means to provide for handling in spaced relation from the pH indicating means.

2. The method of claim 1 including subsequently observing the color of said pH indicating means in comparison with color comparison measurement means.

3. The method of using vaginal probe apparatus for a test purpose associated with need for change in estrogen or estradiol dosage, the steps that include
    a) providing a longitudinally elongated support including a probe insertible into the vagina, for said test purpose, said probe provided to have a flat side,
    b) the support having a portion projecting away from the probe,
    c) said portion including a handle, that is manually manipulable externally of the vagina,
    d) and including inserting said probe into the vagina to an extent to achieve said test purpose associated with a pH indicator provided at said flat side of the probe, said indicator having thickness along said probe flat side that is substantially less than the probe thickness at said flat side,
    e) and withdrawing said probe and said indicator from the vagina for use of said indicator to complete said test purpose,
    f) said flat side protecting away from the pH indicator to enable handling in spaced relation from the pH indicator.

4. The combination of claim 3 including grasping said handle rearward of said indicator during said steps d) and e).

5. The method of claim 3 wherein said indicator is provided to assume a characteristic color in the presence of moisture and at pH 4.5.

6. The method of claim 5 wherein said indicator is provided in the form of a Nitrazine® strip, and said characteristic color is sunflower yellow.

* * * * *